US012788279B2

(12) United States Patent
Wada et al.

(10) Patent No.: US 12,788,279 B2
(45) Date of Patent: Nov. 10, 2026

(54) PHYSICAL-ABILITY ESTIMATION SYSTEM, PHYSICAL-ABILITY ESTIMATION METHOD, AND RECORDING MEDIUM

(71) Applicant: Panasonic Intellectual Property Management Co., Ltd., Osaka (JP)

(72) Inventors: Kengo Wada, Osaka (JP); Takahiro Hiyama, Chiba (JP); Yoshihiro Matsumura, Osaka (JP); Taichi Hamatsuka, Osaka (JP); Takahiro Aihara, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 388 days.

(21) Appl. No.: 18/290,310

(22) PCT Filed: Mar. 29, 2022

(86) PCT No.: PCT/JP2022/015590
§ 371 (c)(1),
(2) Date: Nov. 13, 2023

(87) PCT Pub. No.: WO2022/249746
PCT Pub. Date: Dec. 1, 2022

(65) Prior Publication Data

US 2024/0260854 A1 Aug. 8, 2024

(30) Foreign Application Priority Data

May 27, 2021 (JP) ................................ 2021-088873

(51) Int. Cl.
*A61B 5/11* (2006.01)
*A61B 5/00* (2006.01)
(Continued)

(52) U.S. Cl.
CPC ............ *A61B 5/112* (2013.01); *A61B 5/1071* (2013.01); *A61B 5/1079* (2013.01);
(Continued)

(58) Field of Classification Search
CPC ..................................................... A61B 5/112
See application file for complete search history.

(56) References Cited

U.S. PATENT DOCUMENTS

2015/0325004 A1 11/2015 Utsunomiya et al.
2017/0231532 A1 8/2017 Chakravarty et al.
(Continued)

FOREIGN PATENT DOCUMENTS

CN 108921062 A 11/2018
JP 2008-173250 A 7/2008
(Continued)

OTHER PUBLICATIONS

International Search Report for corresponding Application No. PCT/JP2022/015590, mailed Jun. 21, 2022.
(Continued)

*Primary Examiner* — Marjan Fardanesh
(74) *Attorney, Agent, or Firm* — Renner, Otto, Boisselle & Sklar, LLP

(57) ABSTRACT

A physical-ability estimation system (1) Includes: an analyzer (32) that estimates a gait feature of a user (U) from a moving image generated by capturing the user (U) walking; and an estimator (33) that estimates, based on the gait feature, respective assessment results on at least two assessment Items for assessing a physical ability of the user.

11 Claims, 9 Drawing Sheets

(51) Int. Cl.
*A61B 5/107* (2006.01)
*G06T 7/20* (2017.01)
*G06T 7/73* (2017.01)

(52) U.S. Cl.
CPC .......... *A61B 5/1127* (2013.01); *A61B 5/4023* (2013.01); *G06T 7/20* (2013.01); *G06T 7/73* (2017.01); *G06T 2207/30004* (2013.01); *G06T 2207/30196* (2013.01); *G06T 2207/30204* (2013.01)

(56) References Cited

U.S. PATENT DOCUMENTS

| | | | | |
|---|---|---|---|---|
| 2017/0360335 | A1 | 12/2017 | Washizawa et al. | |
| 2020/0405216 | A1 * | 12/2020 | Matsumura .......... | A61B 5/1121 |

FOREIGN PATENT DOCUMENTS

| | | | |
|---|---|---|---|
| JP | 2010-17447 | A | 1/2010 |
| JP | 2016-140591 | A | 8/2016 |
| JP | 2017-6305 | A | 1/2017 |
| JP | 2017-140393 | A | 8/2017 |
| JP | 2018-69035 | A | 5/2018 |
| JP | 6334925 | B2 | 5/2018 |
| JP | 2019-204451 | A | 11/2019 |
| WO | 2016/139844 | A1 | 9/2016 |

OTHER PUBLICATIONS

Written Opinion for corresponding Application No. PCT/JP2022/015590, mailed Jun. 21, 2022.

International Preliminary Report on Patentability for corresponding Application No. PCT/JP2022/015590, mailed Nov. 15, 2022.

Fay B. Horak, et al., “The Balance Evaluation Systems Test (BESTest) to Differentiate Balance Deficits”, Physical Therapy, vol. 89, No. 5, pp. 484-498, May 2009.

Dario Pavllo, et al., “3D human pose estimation in video with temporal convolutions and semi-supervised training,” arXiv: 1811.11742v2 [cs.CV], Mar. 2019.

* cited by examiner

FIG. 5

| Subsystem | Biomechanical constraints | Stability limits and verticality | Postural change | Anticipatory postural adjustments | Sensory function | Stability in gait |
|---|---|---|---|---|---|---|
| Assessment method | Plantar pain or deformity | Verticality and lateral lean in sitting position | Postural change from sitting to standing | Response to disturbance, forward | Sensory integration (on different floor surfaces, with eyes closed) | Able to walk 6 m with stability within 5.5 seconds |
| | Posture | Functional reach forward | Stand on toes | Response to disturbance, backward | | Change in gait speed |
| | Muscular strength of ankle joint and ankle joint range of motion | Functional reach lateral | Stand on one leg ※Normal if stable for 20 seconds or more | Stepping correction, forward | | Walk with head turns |
| | Muscular strength of hip joint and trunk | | Alternate stair touching | Stepping correction, backward | Stand on inclined table, with eyes closed | Walk with pivot turns |
| | Sit on floor and stand up | | Lift arms in standing position | Stepping correction, lateral | | Step over obstacles |
| | | | | | | TUG |
| | | | | | | TUG with dual task |

FIG. 6
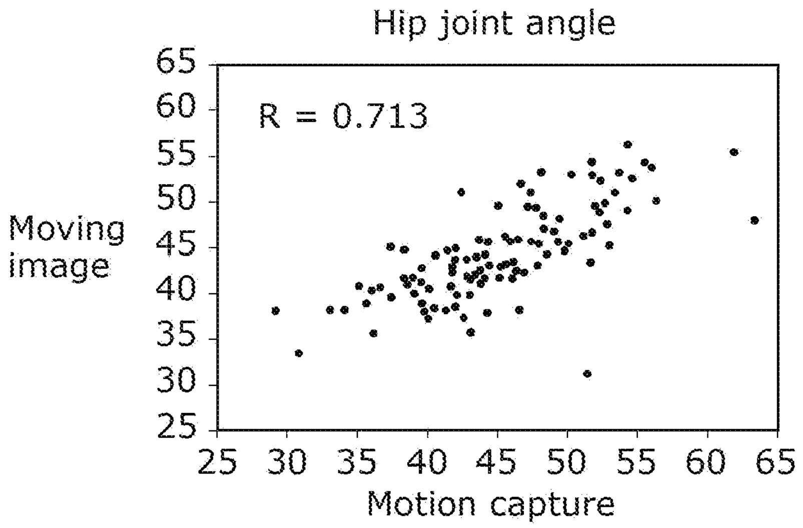
FIG. 7
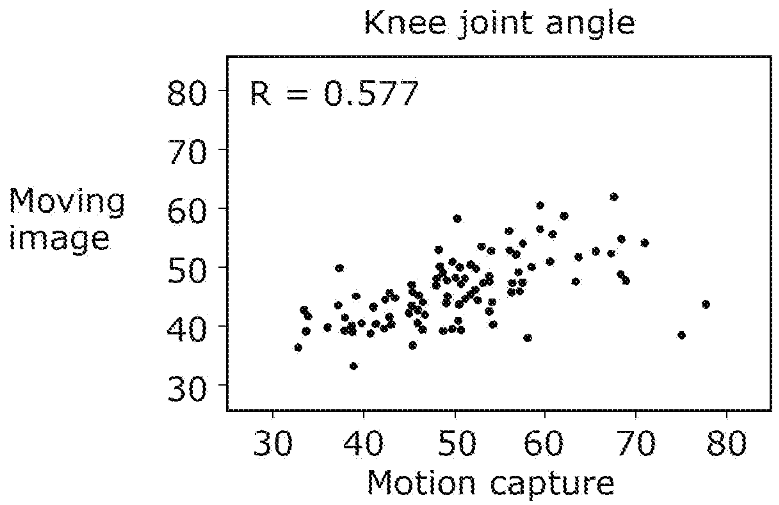
FIG. 8
| | | 1σ | 2σ |
|---|---|---|---|
| Accuracy rate | Hip joint angle | 79.6% | 92.6% |
| | Knee joint angle | 79.6% | 95.4% |

FIG. 9

Estimation of FRT (functional reach)

| | | SVR Linear | SVR RBF | XGboost | Random Forest |
|---|---|---|---|---|---|
| Motion capture | R | 0.61 ±0.03 | 0.44 ±0.07 | 0.53 ±0.05 | 0.56 ±0.04 |
| | MSE | 4.34 ±0.15 | 5.47 ±0.31 | 4.89 ±0.22 | 4.47 ±0.14 |
| Moving image | R | 0.54 ±0.04 | 0.47 ±0.07 | 0.52 ±0.04 | 0.48 ±0.05 |
| | MSE | 4.56 ±0.14 | 5.18 ±0.28 | 4.77 ±0.18 | 4.81 ±0.18 |

FIG. 10

Estimation of time of standing on one leg with eyes open

| | | SVR Linear | SVR RBF | XGboost | Random Forest |
|---|---|---|---|---|---|
| Motion capture | R | 0.45 ±0.02 | 0.28 ±0.04 | 0.31 ±0.05 | 0.35 ±0.04 |
| | MSE | 1.33 ±0.03 | 1.56 ±0.05 | 1.50 ±0.06 | 1.44 ±0.05 |
| Moving image | R | 0.31 ±0.03 | 0.17 ±0.04 | 0.36 ±0.04 | 0.29 ±0.04 |
| | MSE | 1.45 ±0.03 | 1.60 ±0.06 | 1.43 ±0.06 | 1.46 ±0.03 |

FIG. 11

Estimation of ratio of standing on one leg with eyes open to standing on one leg with eyes closed

| | | SVR Linear | SVR RBF | XGboost | Random Forest |
|---|---|---|---|---|---|
| Motion capture | R | 0.34 ±0.05 | 0.32 ±0.04 | 0.37 ±0.05 | 0.39 ±0.05 |
| | MSE | 1.15 ±0.04 | 1.25 ±0.07 | 1.15 ±0.03 | 1.10 ±0.03 |
| Moving image | R | 0.24 ±0.05 | 0.12 ±0.06 | 0.32 ±0.04 | 0.32 ±0.05 |
| | MSE | 1.22 ±0.03 | 1.33 ±0.06 | 1.18 ±0.03 | 1.15 ±0.02 |

FIG. 12

Estimation of TUG

| | | SVR Linear | SVR RBF | XGboost | Random Forest |
|---|---|---|---|---|---|
| Motion capture | R | 0.54 ±0.03 | 0.45 ±0.03 | 0.49 ±0.03 | 0.52 ±0.04 |
| | MSE | 0.62 ±0.02 | 0.69 ±0.03 | 0.64 ±0.01 | 0.61 ±0.02 |
| Moving image | R | 0.49 ±0.03 | 0.49 ±0.05 | 0.53 ±0.03 | 0.56 ±0.03 |
| | MSE | 0.64 ±0.02 | 0.67 ±0.04 | 0.63 ±0.02 | 0.61 ±0.02 |

FIG. 13

Estimation about whether healthy or suffering from MCI (the number of gait features: 10)

| | | SVR Linear | SVR RBF | XGboost | Random Forest |
|---|---|---|---|---|---|
| Motion capture | AUC | 0.52 ±0.06 | 0.51 ±0.04 | 0.61 ±0.05 | 0.68 ±0.04 |
| Moving image | AUC | 0.50 ±0.06 | 0.47 ±0.04 | 0.62 ±0.07 | 0.57 ±0.04 |

FIG. 14

Estimation about whether healthy or suffering from MCI (gait characteristic: only gait speed)

| | | SVR Linear | SVR RBF | XGboost |
|---|---|---|---|---|
| Motion capture | AUC | 0.47 ±0.06 | 0.72 ±0.03 | 0.78 ±0.05 |
| Moving image | AUC | 0.56 ±0.12 | 0.56 ±0.05 | 0.65 ±0.04 |

PHYSICAL-ABILITY ESTIMATION SYSTEM, PHYSICAL-ABILITY ESTIMATION METHOD, AND RECORDING MEDIUM

TECHNICAL FIELD

The present invention relates to a physical-ability estimation system, a physical-ability estimation method, and a recording medium.

BACKGROUND ART

Recent years have seen the development of methods for assessing or determining, based on image data, a physical ability associated with risk of falling for instance. For example, Patent Literature (PTL) 1 discloses a technology of analyzing image data to calculate gait parameters and computing information about assessment of gait movement.

CITATION LIST

Patent Literature

[PTL 1]

Japanese Unexamined Patent Application Publication No. 2016-140591

SUMMARY OF INVENTION

Technical Problem

The method disclosed in PTL 1 is able to assess the physical ability (for example, assess gait movement). However, if there is a problem with the physical ability, the method is unable to find out a factor responsible for this problem.

In response to this, the present invention provides a physical-ability estimation system, a physical-ability estimation method, and a recording medium that are capable of estimating a factor responsible for a problem with a physical ability.

Solution to Problem

According to an aspect of the present invention, a physical-ability estimation system includes: a first estimator that estimates a gait feature of a user from a moving image generated by capturing the user walking; and a second estimator that estimates, based on the gait feature, respective assessment results on at least two assessment items for assessing a physical ability of the user.

According to another aspect of the present invention, a physical-ability estimation method includes: estimating a gait feature of a user from a moving image generated by capturing the user walking; and estimating, based on the gait feature, respective assessment results on at least two assessment items for assessing a physical ability of the user.

According to still another aspect of the present invention, a non-transitory computer-readable recording medium having recorded thereon a computer program for causing a computer to execute the above-described physical-ability estimation method.

Advantageous Effects of Invention

A physical-ability estimation system according to an aspect of the present invention is capable of estimating a factor responsible for a problem with a physical ability.

BRIEF DESCRIPTION OF DRAWINGS

FIG. 5 is a diagram illustrating a subsystem that provides specifics of the balance ability.

FIG. 6 is a diagram illustrating a correlation between motion capture and moving image in hip joint angle estimation, according to Embodiment.

FIG. 7 is a diagram illustrating a correlation between motion capture and moving image in knee joint angle estimation, according to Embodiment.

FIG. 8 is a diagram illustrating an accuracy rate of estimation of normal range of gait motion based on a moving image, according to Embodiment.

FIG. 9 is a diagram illustrating a correlation between motion capture and moving image in FRT estimation, according to Embodiment.

FIG. 10 is a diagram illustrating a correlation between motion capture and moving image in estimation of time of standing on one leg with eyes open, according to Embodiment.

FIG. 11 is a diagram illustrating a correlation between motion capture and moving image in estimation of a ratio of standing on one leg with eyes open to standing on one leg with eyes closed, according to Embodiment.

FIG. 12 is a diagram illustrating a correlation between motion capture and moving image in TUG estimation, according to Embodiment.

FIG. 13 is a diagram illustrating an assessment result of estimation about whether a user is healthy or suffering from MCI based on motion capture and moving image (the number of gait features: 10), according to Embodiment.

FIG. 14 is a diagram illustrating an assessment result of estimation about whether a user is healthy or suffering from MCI based on motion capture and moving image (gait characteristic: only the gait speed), according to Embodiment.

DESCRIPTION OF EMBODIMENT

Hereinafter, a certain exemplary embodiment will be described in detail with reference to the accompanying Drawings.

It should be noted that the following embodiment is a general or specific example of the present invention. The numerical values, shapes, elements, arrangement and connection configuration of the elements, steps, the order of the steps, etc., described in the following embodiment are merely examples, and are not intended to limit the present invention. Among elements in the following embodiment, those not described in any one of the independent claims are described as optional elements.

It should also be noted that the respective figures are schematic diagrams and are not necessarily precise illustrations. Therefore, the scales or the like applied in the figures are not necessarily unified. Additionally, elements that are essentially the same share like reference signs in the figures. Accordingly, overlapping explanations thereof are omitted or simplified.

It should also be noted that the following description may include expressions, such as the same, to indicate relationships between the elements, and also numerical values and their ranges. However, such expressions, numerical values, and ranges do not mean exact meanings only. They also mean the substantially same ranges including a difference of, for example, about several % (for example, about 5%) from the completely same range.

Embodiment

The following describes a physical-ability estimation system according to the present embodiment, with reference to FIG. 1 to FIG. 14.

[1. Configuration of Physical-Ability Estimation System]

Figure 1:
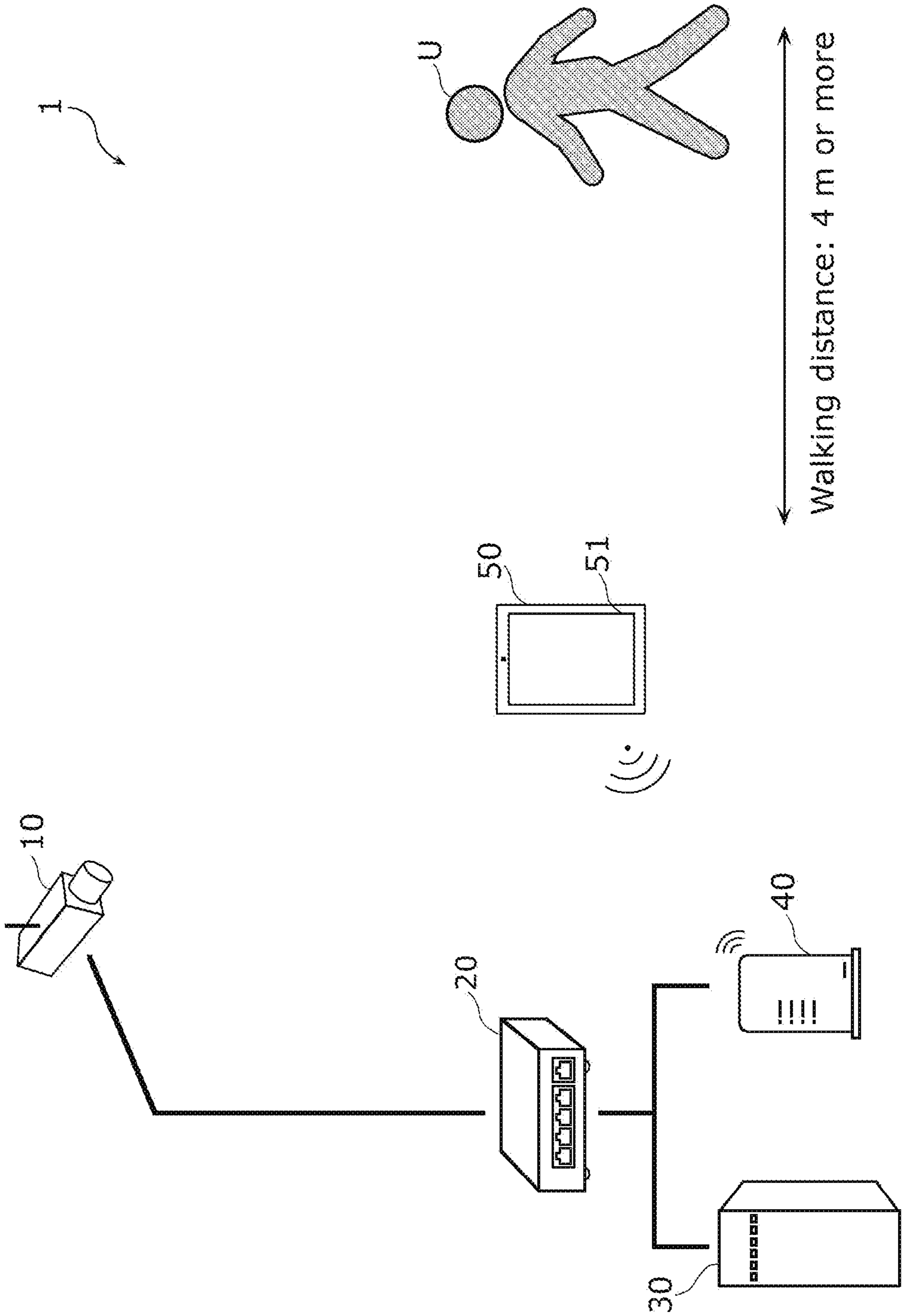
FIG. 1 is a schematic diagram illustrating a configuration of a physical-ability estimation system according to Embodiment.

First, a configuration of the physical-ability estimation system according to the present embodiment is described with reference to FIG. 1 and FIG. 2. FIG. 1 is a schematic diagram illustrating a configuration of physical-ability estimation system 1 according to the present embodiment.

As illustrated in FIG. 1, physical-ability estimation system 1 includes imaging device 10, hub 20, control device 30, router 40, and terminal device 50.

Imaging device 10 images user U who is walking. For example, imaging device 10 obtains a moving image (video) by imaging user U walking a predetermined distance. The predetermined distance is 4 m or more for example, but is not limited to this distance.

Imaging device 10 is placed in a building, such as a care facility, a hospital, an office, or a public institution. Imaging device 10 may be placed in a house. To be more specific, imaging device 10 is a security camera (a monitoring camera), and may be a door phone (intercom) camera. Physical-ability estimation system 1 may include any number of imaging devices 10, and may include a plurality of imaging devices 10. Imaging devices 10 may be a plurality of cameras included in a motion capture system.

Note that imaging device 10 may be a universal serial bus (USB) camera or a camera included in terminal device 50 (such as a tablet camera or a smartphone camera). Imaging device 10 may be any camera that is capable of capturing moving images. Imaging device 10 may be a fixed or portable camera. Physical-ability estimation system 1 may also include, instead of or in addition to imaging device 10, a sensor capable of obtaining a gait feature. Examples of the sensor capable of obtaining the gait feature include, but are not limited to, a distance sensor, a Wifi sensor, and an acceleration sensor.

Note that gait is a manner of body movements made by a person during walking. The gait feature indicating the gait include a gait cycle, a gait speed, a stride length, a step length, and a step width. The gait feature may also include respective values obtained by dividing the stride length, the step length, and the step width by the height. The gait feature may also include a value obtained by dividing the stride length by the step length.

Hub 20 is connected to imaging device 10, control device 30, and router 40, and relays communications between these devices.

Control device 30 estimates the physical ability of user U, based on the moving image captured by imaging device 10. Control device 30 estimates the gait feature of user U based on the moving image captured by imaging device 10. Then, based on the estimated gait feature, control device 30 estimates a score for each of at least two assessment items on the physical ability. The at least two assessment items, which are described in detail later, relate to physical ability levels. For example, the at least two assessment items include at least one of: a balance-related assessment item; a flexibility-related assessment item; and muscle-strength-related assessment item. The following describes a case where each of the at least two assessment items is related to balance. Note that although the score is represented by a numerical value from 0 to 100, this is not intended to be limiting. The score may be represented by a value normalized corresponding to an assessment item.

Router 40 relays communications between terminal device 50 and a network connected to hub 20.

Terminal device 50 includes display 51 and a receiver (not shown). Terminal device 50 displays a result of the estimation of the physical ability to user U or receives an input of predetermined information from user U. The predetermined information may be biological information on user U, for example. The biological information includes at least one of the gender, the height, and the weight of user U. In other words, the biological information includes physical information on user U, such as the height and the weight.

Display 51 is implemented by a liquid crystal panel or an organic electroluminescent (organic EL) panel, for example. Display 51 is an example of a presenter that presents predetermined information to the user. The presenter is not limited to display 51 and may be implemented by a sound producer, such as a speaker. The receiver includes a touch panel and buttons, and may have a configuration to obtain information from the user by voice or gestures.

Terminal device 50 is a portable terminal, such as a tablet or a smartphone. However, terminal device 50 may be a stationary terminal.

As described above, physical-ability estimation system 1 estimates the gait feature based on the moving image that captures user U walking and, based on the estimated gait feature, estimates the score for each of the at least two assessment items on the physical ability. Physical-ability estimation system 1 estimates the score in the assessment item related to the physical ability level, from the gait feature, To be more specific, physical-ability estimation system 1 estimates a frail state of user U (an elderly person, for example) from the manner of walking. Physical-ability estimation system 1 is capable of estimating the physical ability of an elderly person who is lively and thus does not appear to be frail.

Note that although the communication between the devices included in physical-ability estimation system 1 is established via hub 20 and router 40, this is not intended to be limiting. The method of communication between the devices is not limited to any particular methods.

Figure 2:
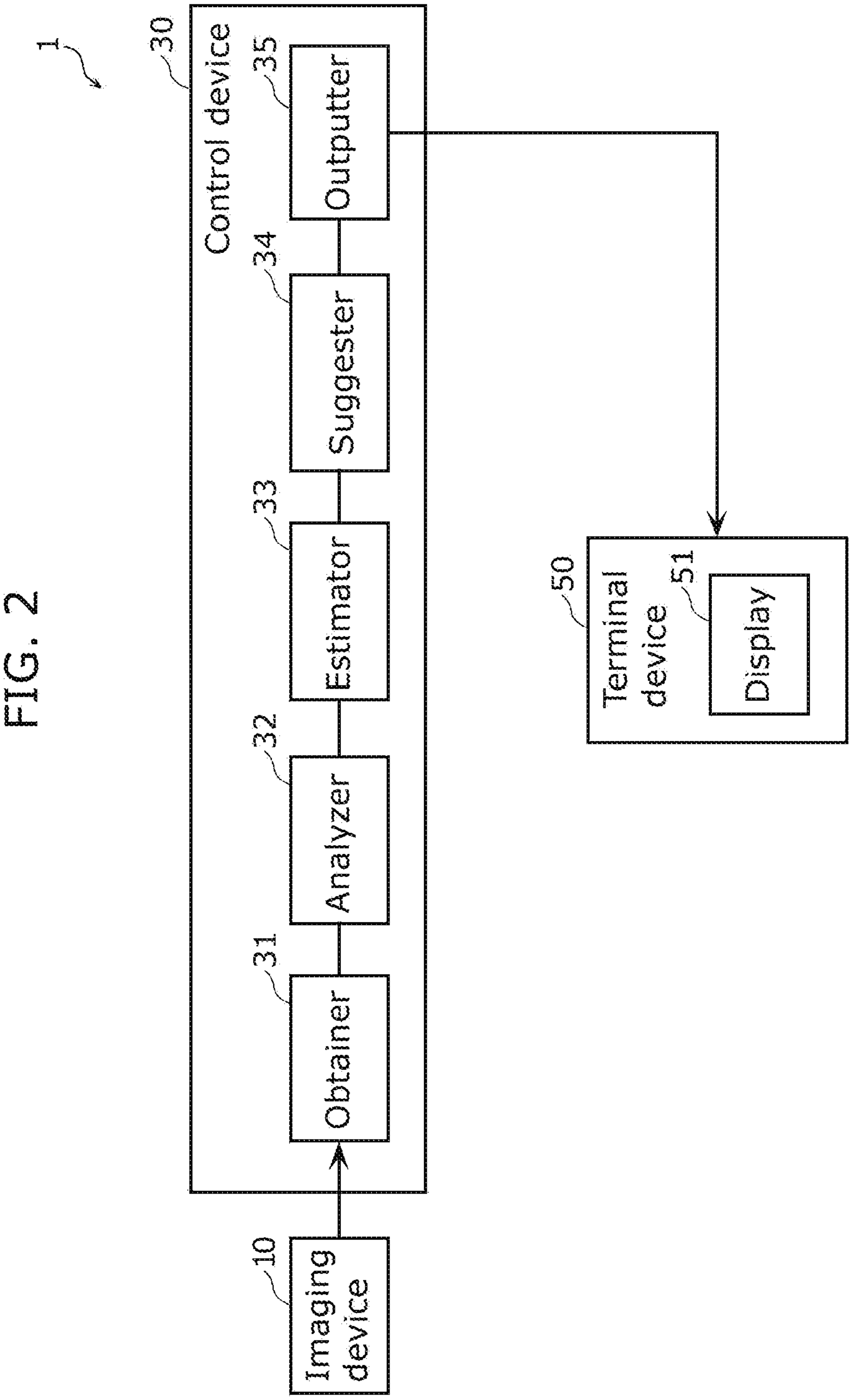
FIG. 2 is a block diagram illustrating a functional configuration of the physical-ability estimation system according to Embodiment.

FIG. 2 is a block diagram illustrating a functional configuration of physical-ability estimation system 1 according to the present embodiment. Note that hub 20 and router 40 illustrated in FIG. 1 are omitted from FIG. 2.

As illustrated in FIG. 2, control device 30 includes obtainer 31, analyzer 32, estimator 33, suggester 34, and outputter 35.

Obtainer 31 obtains the moving image that captures user U walking, from imaging device 10. Obtainer 31 includes a communication circuit.

Analyzer 32 estimates the gait feature of user U, based on the moving image obtained by obtainer 31. To be more specific, analyzer 32 estimates a frame of user U based on the moving image and, based on the estimated frame (frame estimation data), estimates the gait feature of user U.

Analyzer 32 estimates the gait feature of user U from the moving image that captures user U walking. For example, analyzer 32 estimates the frame of user U from user U shown in the moving image and, based on the estimated frame, estimates the gait feature. For example, analyzer 32 determines a three-dimensional frame model (three-dimensional coordinate data on human joints, such as knee joint, hip joint, and ankle) of user U shown in the moving image, using an existing algorithm. Then, analyzer 32 determines (estimates) the gait feature, based on changes of positions of skeletal points of the three-dimensional frame model. Note that analyzer 32 may estimate a two-dimensional frame model of user U shown in the moving image. Analyzer 32 is an example of a first estimator.

The existing algorithm is used for a machine learning model. In the present embodiment, the existing algorithm is an existing frame estimation model that is, for example, a learned convolutional neural network (CNN) model trained for time-series estimation. The frame estimation model is trained using "Human3.6" dataset, for example. Furthermore, the frame estimation model is trained to be able to detect a frame with a margin of error of about 25 mm to about 30 mm. The frame estimation model may be trained using a moving image corresponding to 27 frames, for example.

Note that analyzer 32 may estimate the gait feature based on the moving image (for example, a plurality of distance images) obtained by motion capture. In this case, user U wears markers (reflectors, for example). Thus, user U walking with these markers on is shown in the moving image. Analyzer 32 may estimate the gait feature based on the markers shown in this moving image (for example, based on temporal changes of the positions of the markers).

Estimator 33 estimates results on the at least two assessment items on the physical ability, based on the gait feature estimated by analyzer 32. For example, estimator 33 estimates a score of user U for each of the at least two assessment items, based on the gait feature estimated by analyzer 32. To be more specific, estimator 33 obtains, as a score for each of the at least two assessment items, an output from the learned model as a result of inputting the gait feature into the learned model. Estimator 33 may estimate a score of user U for each of the at least two assessment items, based on at least one of the biological information (biological feature) of user U and environmental information (environmental feature) indicating a walk environment of user U. Estimator 33 is an example of a second estimator.

Suggester 34 determines suggestions made for user U to prevent further decline of the physical ability, based on the estimation result from estimator 33. Suggester 34 determines the suggestions according to the individual scores in the at least two assessment items. The suggestions include exercise, diet, and seeking medical attention. Suggester 34 determines the suggestions by reference to a table that associates each of the scores on the at least two assessment items with a suggestion. This enables physical-ability estimation system 1 to suggest an intervention-effective method for user U.

Outputter 35 outputs the estimation result received from estimator 33 and the suggestions made by suggester 34, to terminal device 50. For example, outputter 35 outputs information to be displayed by display 51 of terminal device 50. Outputter 35 includes a communication circuit.

[2. Operation of Physical-Ability Estimation System]

Figure 3:
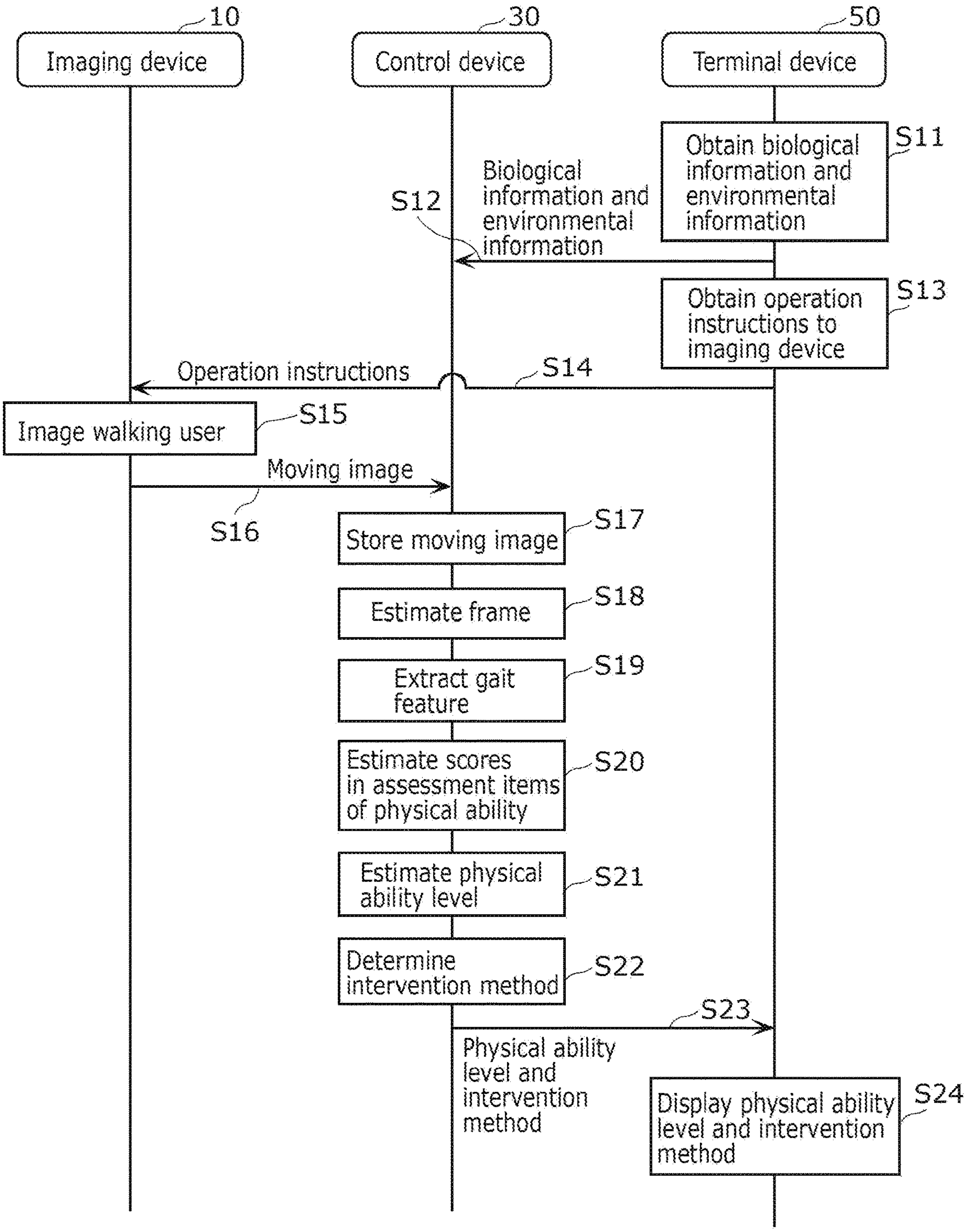
FIG. 3 is a flowchart of an operation performed by the physical-ability estimation system according to Embodiment.
Figure 4:
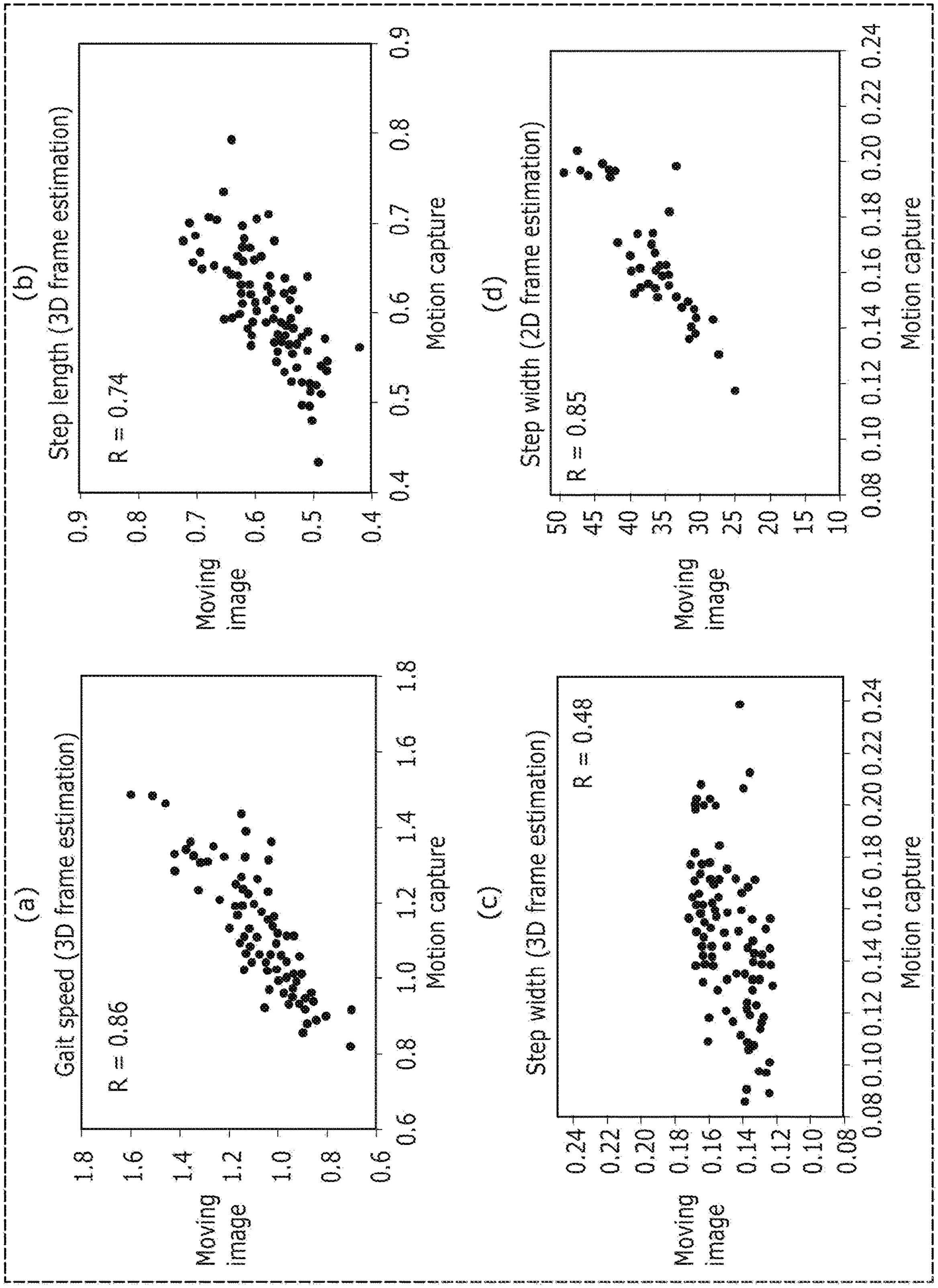
FIG. 4 is a diagram illustrating a correlation between motion capture and moving image in frame estimation, according to Embodiment.

The following describes an operation of physical-ability estimation system 1 having the above configuration, with reference to FIG. 3 to FIG. 5. FIG. 3 is a flowchart of the operation performed by physical-ability estimation system 1 according to the present embodiment.

As illustrated in FIG. 3, terminal device 50 obtains the biological information and the environmental information via the receiver (S11). For example, terminal device 50 obtains the biological information from user U via the receiver. Furthermore, terminal device 50 obtains the environmental information including a state of a surface on which user U walks (a road surface, for example) and a thing being carried by user U (the presence or absence of a bag, for example).

Next, terminal device 50 outputs the obtained biological information and the environmental information to control device 30, and control device 30 obtains the biological information and the environmental information via obtainer 31 (S12).

Next, terminal device 50 obtains operation instructions to imaging device 10, from user U via the receiver (S13). The operation instructions include an instruction to start imaging, for example.

Next, terminal device 50 outputs the obtained operation instructions to imaging device 10, and imaging device 10 obtains the operation instructions (S14).

Next, imaging device 10 images user U walking (S15). For example, imaging device 10 images user U walking 4 m or more. Imaging device 10 performs imaging to capture the whole body of user U, for example.

Next, imaging device 10 outputs the moving image obtained as a result of the imaging to control device 30, and control device 30 obtains the moving image via obtainer 31 (S16). Control device 30 stores the obtained moving image into a storage (not shown) (S17).

Next, analyzer 32 of control device 30 estimates the frame of user U based on the obtained moving image (S18). Control device 30 receives an output obtained as a result of inputting the obtained moving image into an existing frame estimation model. Control device 30 obtains this output as positions of the skeletal points of a three-dimensional frame model. Analyzer 32 may also obtain a two-dimensional frame model (two-dimensional coordinate data on human joints, such as knee joint, hip joint, and ankle) of user U shown in the moving image, using an existing algorithm.

Next, analyzer 32 of control device 30 extracts the gait feature of user U, based on changes of the positions of the skeletal points of the three-dimensional frame model (S19). In other words, analyzer 32 estimates the gait feature of user U, based on the changes of the positions of the skeletal points of the three-dimensional frame model.

FIG. 4 is a diagram illustrating correlations between motion capture and moving image in frame estimation, according to the present embodiment. In FIG. 4, the gait feature of user U obtained by motion capture and the gait feature of user U obtained based on the three-dimensional frame model from the moving image are represented by one point. FIG. 4 illustrates the plotted points corresponding to 108 persons, and also indicates correlation coefficients ("R"

in this diagram). In the following, a correlation is determined to be present if a correlation coefficient is 0.5 or higher.

In (a) of FIG. 4, a correlation between the gait speed of user U obtained by motion capture and the gait speed of user U based on the three-dimensional frame model is illustrated. Correlation coefficient R is 0.86. Thus, a correlation is present between the gait speed obtained by motion capture and the gait speed obtained based on the three-dimensional frame model.

In (b) of FIG. 4, a correlation between the step length of user U obtained by motion capture and the step length of user U based on the three-dimensional frame model is illustrated. Correlation coefficient R is 0.74. Thus, a correlation is present between the step length obtained by motion capture and the step length obtained based on the three-dimensional frame model.

In (c) of FIG. 4, a correlation between the step width of user U obtained by motion capture and the step width of user U based on the three-dimensional frame model is illustrated. Correlation coefficient R is 0.48. Thus, a low correlation is present between the step width obtained by motion capture and the step width obtained based on the three-dimensional frame model.

In (d) of FIG. 4, a correlation between the step width of user U obtained by motion capture and the step width of user U based on the two-dimensional frame model is illustrated. Correlation coefficient R is 0.85. Thus, a correlation is present between the step width obtained by motion capture and the step width obtained based on the two-dimensional frame model. On this account, the two-dimensional frame model may be used in the step-length estimation.

As described above, there is a correlation between the gait feature based on motion capture and the gait feature based on the moving image. If the gait feature obtained by motion capture is correct, the gait feature can be estimated based on the moving image.

Note that in step S19, analyzer 32 may also calculate information indicating variability in the estimated gait feature. The information indicating the variability is a standard deviation, for example. Analyzer 32 calculates the information indicating the variability, based on time-series data on values of the gait feature estimated based on the moving image. Analyzer 32 calculates the variability for each of the gait feature. The information indicating the variability is also included in the gait feature. To be more specific, the gait feature in the present specification may include, in addition to the basic gait feature including the gate cycle, the information indicating the variability in the basic gait feature (that is, variability feature).

Analyzer 32 outputs the estimated gait feature of user U to estimator 33.

Referring back to FIG. 3, estimator 33 of control device 30 next estimates the scores in the assessment items on the physical ability of user U, using the gait feature (S20). Estimator 33 estimates the score for each of the assessment items, using the learned model generated for each of the assessment items.

Here, the assessment items to be estimated by estimator 33 are described with reference to FIG. 5. FIG. 5 is a diagram illustrating a subsystem that provides specifics of the balance ability. FIG. 5 illustrates a relationship between an item of the subsystem and an assessment method for the item. The balance ability relates to fall that is a significant factor in determining the level of long-term care needed or the level of support needed. The assessment based on the balance ability illustrated in FIG. 5 allows an effective intervention related to fall prevention. This raises an expectation of a longer healthy life-span. In FIG. 5, the dashed-line boxes indicate items that can be estimated from the gait feature.

Note that six items illustrated in FIG. 5 indicate six sections proposed by Dr. Horak et al. (Horak FB., Wrisley DM., et al.: The Balance Evaluation Systems Test (BESTest) to Differentiate Balance Deficits. Phys Ther. 2009; 89.5: 484-498).

As illustrated in FIG. 5, the items (examples of a first item) of the subsystem that provides specifics of the balance ability include biomechanical constraints, stability limits and verticality, postural change, anticipatory postural adjustments, sensory function, and stability in gait. Although verification results are described later, the followings are found from FIG. 5.

The joint range of motion (range of motion of a joint) during gait, among the assessment methods for the biomechanical constraints, can be estimated based on the gait feature. More specifically, the hip joint angle and the knee joint angle can be estimated as the joint ranges of motion. Thus, the score in the section of the biomechanical constraints can be estimated based on the gait feature. For example, each of the hip joint angle and the knee joint angle changes with changes in the gait speed. The slower the gait speed, the smaller each of the hip joint angle and the knee joint angle tends to be, for example. On this account, a correlation is present between the gait feature and each of the hip joint angle and the knee joint angle. Each of the hip joint angle and the knee joint angle is an example of an ankle range of motion (range of motion of an ankle).

Estimator 33 receives an output obtained as a result of inputting the gait feature of user U into a first learned model, which is a machine learned model trained to output a hip joint angle for an input of gait feature. Here, estimator 33 obtains this output as an estimated value of the hip joint angle. The gait feature inputted include at least the gait speed. The gait feature inputted may also include at least one of: the gait cycle, stride length, step length, and step width; the respective values obtained by dividing the stride length, the step length, and the step width by the height; and the value obtained by dividing the stride length by the step length. Furthermore, at least one of the biological information and the environmental information may also be inputted into the first learned model.

Estimator 33 receives an output obtained as a result of inputting the gait feature of user U into a second learned model, which is a machine learned model trained to output a knee joint angle for an input of gait feature. Here, estimator 33 obtains this output as an estimated value of the knee joint angle. The gait feature inputted includes at least the gait speed. The gait feature inputted may also include at least one of: the gait cycle, stride length, step length, and step width; the respective values obtained by dividing the stride length, the step length, and the step width by the height; and the value obtained by dividing the stride length by the step length. Furthermore, at least one of the biological information and the environmental information may also be inputted into the second learned model.

Note that the information to be inputted into the first learned model and the second learned model (the input information corresponding to the hip joint angle and the knee joint angle) are preset and stored in, for example, the storage. Estimator 33 extracts the preset information as the input information, based on the biological information and the environmental information obtained in Step S12 and the gait feature obtained in Step S19. Then, estimator 33 inputs the extracted input information into the first learned model and the second learned model. The information inputted into the first learned model and the information inputted into the second learned model may be the same or different from each other.

The following describes the stability limits and verticality. The forward Functional Reach Test (FRT), among the assessment methods for the stability limits and verticality, can be estimated based on the gait feature. More specifically, the score in the section of the stability limits and verticality can be estimated based on the gait feature. To estimate the functional reach forward, the height and the gait speed, for example, are considered important.

Estimator 33 receives an output obtained as a result of inputting the biological information (the physical information, for example) of user U and the gait feature of user U into a third learned model, which is a machine learned model trained to output a value of the functional reach forward for an input of biological information and gait feature. Here, estimator 33 obtains this output as an estimated value of the functional reach forward. The biological information inputted includes at least the height. The biological information inputted may also include at least one of the gender, the weight, and the age. The gait feature inputted includes at least the gait speed. The gait feature inputted may also include at least one of: the gait cycle, stride length, step length, and step width; the respective values obtained by dividing the stride length, the step length, and the step width by the height; and the value obtained by dividing the stride length by the step length. Furthermore, the environmental information may also be inputted into the second learned model.

Note that the information to be inputted into the third learned model (the input information corresponding to the functional reach forward) is preset and stored in, for example, the storage. Estimator 33 extracts the preset information as the input information, based on the biological information and the environmental information obtained in Step S12 and the gait feature obtained in Step S19. Then, estimator 33 inputs the extracted input information into the third learned model.

The following describes the postural change. Standing on one leg (normal if stable for 20 seconds or more, for example), among the assessment methods for the postural change, can be estimated based on the gait feature. More specifically, the score in the section of the postural change can be estimated based on the gait feature. In the present embodiment, time of standing on one leg with eyes open is estimated as an indicator for the postural change. To estimate the time of standing on one leg with eyes open, the height and the gait speed, for example, are considered important.

Estimator 33 receives an output obtained as a result of inputting the biological information (the physical information, for example) of user U and the gait feature of user U into a fourth learned model, which is a machine learned model trained to output time of standing on one leg with eyes open for an input of biological information and gait feature. Here, estimator 33 obtains this output as an estimated value of the time of standing on one leg with eyes open. The biological information inputted includes at least the height. The biological information inputted may also include at least one of the gender, the weight, and the age. The gait feature inputted includes at least the gait speed. The gait feature inputted may also include at least one of: the gait cycle, stride length, step length, and step width; the respective values obtained by dividing the stride length, the step length, and the step width by the height; and the value obtained by dividing the stride length by the step length.

Furthermore, the gait feature inputted may also include information indicating variability in the gait feature. The information indicating the variability in the gait feature includes information indicating variability in an item of the gait characteristic inputted. For example, this information includes at least information indicating variability in the gait speed. The information indicating the variability in the gait feature may also include information indicating variability in at least one of: the gait cycle, stride length, step length, and step width; the respective values obtained by dividing the stride length, the step length, and the step width by the height; and the value obtained by dividing the stride length by the step length. Furthermore, the environmental information may also be inputted into the fourth learned model.

Note that the information to be inputted into the fourth learned model (the input information corresponding to the time of standing on one leg with eyes open) is preset and stored in, for example, the storage. Estimator 33 extracts the preset information as the input information, based on the biological information and the environmental information obtained in Step S12 and the gait feature obtained in Step S19. Then, estimator 33 inputs the extracted input information into the fourth learned model.

The following describes the sensory function. Standing on an inclined table with eyes closed, among the assessment methods for the sensory function, can be estimated based on the gait feature. More specifically, the score in the section of the sensory function can be estimated based on the gait feature. In the present embodiment, a ratio of standing on one leg with eyes open to standing on one leg with eyes closed is estimated as an indicator for the sensory function. The ratio of the standing on one leg with eyes open to the standing on one leg with eyes closed is based on the time of standing on one leg with eyes open and the time of standing on one leg with eyes closed. For example, this ratio may be time (time of standing on one leg) logarithmically transformed by log 2 (time of standing on one leg with eyes open/time of standing on one leg with eyes closed). To estimate the ratio of the standing on one leg with eyes open to the standing on one leg with eyes closed, the height and the gait speed, for example, are considered important.

Estimator 33 receives an output obtained as a result of inputting the biological information (the physical information, for example) of user U and the gait feature of user U into a fifth learned model, which is a machine learned model trained to output a ratio of standing on one leg with eyes open to standing on one leg with eyes closed for an input of biological information and gait feature. Here, estimator 33 obtains this output as an estimated value of the ratio of the standing on one leg with eyes open to the standing on one leg with eyes closed. The biological information inputted includes at least the height. The biological information inputted may also include at least one of the gender, the weight, and the age. The gait feature inputted includes at least the gait speed. The gait feature inputted may also include at least one of: the gait cycle, stride length, step length, and step width; the respective values obtained by dividing the stride length, the step length, and the step width by the height; and the value obtained by dividing the stride length by the step length.

Furthermore, the gait feature inputted may also include information indicating variability in the gait feature. The information indicating the variability in the gait feature includes information indicating variability in an item of the gait characteristic inputted. For example, this information includes at least information indicating variability in the gait speed. The information indicating the variability in the gait feature may also include information indicating variability in at least one of: the gait cycle, stride length, step length, and step width; the respective values obtained by dividing the stride length, the step length, and the step width by the height; and the value obtained by dividing the stride length by the step length. Furthermore, the environmental information may also be inputted into the fifth learned model.

Note that the information to be inputted into the fifth learned model (the input information corresponding to the ratio of the standing on one leg with eyes open to the standing on one leg with eyes closed) is preset and stored in, for example, the storage, Estimator 33 extracts the preset information as the input information, based on the biological information and the environmental information obtained in Step S12 and the gait feature obtained in Step S19. Then, estimator 33 inputs the extracted input information into the fifth learned model. The input information inputted to the fifth learned model may be the same as the input information inputted to the fourth learned model.

Note that estimator 33 may estimate (calculate, for example) the ratio of the standing on one leg with eyes open to the standing on one leg with eyes closed, based on: the estimated value of the time of standing on one leg with eyes open that is the output from the fourth learned model; and an estimated value of the time of standing on one leg with eyes closed that is an output obtained as a result of inputting the biological information (the physical information, for example) of user U and the gait feature of user U obtained based on the moving image into a learned model. This learned model is a machine learned model trained to output time of standing on one leg with eyes closed for an input of biological information and gait feature.

The following describes the stability in gait. Timed Up to Go (TUG), among the assessment methods for the stability in gait, can be estimated based on the gait feature. Furthermore, whether the user is suffering from mild cognitive impairment (MCI) can be estimated based on the gait feature. In the present embodiment, the score in the section of the stability in gait is estimated based on an estimated value of TUG time and an estimation result on MCI. More specifically, the score in the section of the stability in gait can be estimated based on the gait feature. To estimate the TUG time, the age, the step length, and the stride length, for example, are considered important. To estimate MCI, the gait speed for example is considered important and the age is also assumed to be important. Note that the estimation result on MCI indicates whether the user is healthy or suffering from MCI.

Estimator 33 receives an output obtained as a result of inputting the biological information (the physical information, for example) of user U and the gait feature of user U obtained based on the moving image into a sixth learned model, which is a machine learned model trained to output TUG time for an input of biological information and gait feature. Here, estimator 33 obtains this output as an estimated value of TUG. The biological information inputted includes at least the age. The biological information inputted may also include at least one of the gender, the height, and the weight. The gait feature inputted includes at least the step length and the stride length. The gait feature inputted may also include at least one of: the gait cycle, gait speed, and step width; the respective values obtained by dividing the stride length, the step length, and the step width by the height; and the value obtained by dividing the stride length by the step length. Furthermore, the environmental information may also be inputted into the sixth learned model.

Note that the information to be inputted into the sixth learned model (the input information corresponding to TUG) is preset and stored in, for example, the storage. Estimator 33 extracts the preset information as the input information, based on the biological information and the environmental information obtained in Step S12 and the gait feature obtained in Step S19. Then, estimator 33 inputs the extracted input information into the sixth learned model. The input information inputted to the sixth learned model may be the same as the input information inputted to the third learned model.

Estimator 33 receives an output obtained as a result of inputting the biological information (the physical information, for example) of user U and the gait feature of user U obtained based on the moving image into a seventh learned model, which is a machine learned model trained to output a determination result on MCI for an input of biological information and gait feature. Here, estimator 33 obtains this output as an estimation result on MCI. The biological information inputted includes at least one of the gender, the height, the weight, and the age. The gait feature inputted includes at least the gait speed. The gait feature inputted may also include at least one of: the gait cycle, stride length, step length, and step width; the respective values obtained by dividing the stride length, the step length, and the step width by the height; and the value obtained by dividing the stride length by the step length. The gait feature inputted may include only the gait speed, for example. Furthermore, the environmental information may also be inputted into the seventh learned model.

Note that the information to be inputted into the seventh learned model (the input information corresponding to MCI) is preset and stored in, for example, the storage. Estimator 33 extracts the preset information as the input information, based on the biological information and the environmental information obtained in Step S12 and the gait feature obtained in Step S19. Then, estimator 33 inputs the extracted input information into the seventh learned model.

As described above, using a learned model (a machine learned model) that is previously trained by machine learning depending on a value to be estimated (or a determination result), estimator 33 estimates this value (for example, a value described above, such as the hip joint angle (or the determination result)) from at least the gait feature.

Note that examples of the assessment item on the physical ability include: at least one of the hip joint angle and the knee joint angle; the FRT; the time of standing on one leg with eyes open; the ratio of the standing on one leg with eyes open to the standing on one leg with eyes closed; and at least one of TUG and MCI. Estimator 33 estimates at least two of five assessment items. For example, the at least two assessment items may include at least two of: the ankle range of motion; the FRT; the standing on one leg with eyes open; the standing on one leg with eyes closed; and TUG. Estimator 33 may estimate an estimated value as a score in the assessment item. Alternatively, estimator 33 may estimate, as the score, a value corresponding to the estimated value (or the estimation result) by reference to a table that associates an estimated value (or an estimation result) with a score.

Next, estimator 33 estimates the physical ability level of user U, based on the score in the assessment item on the physical ability (S21). Estimator 33 estimates an ability level for each of the biomechanical constraints, the stability limits and verticality, the postural change, the sensory function, and the stability in gait, which are the items of the subsystem that provides specifics of the balance ability. For example, based on at least one of the scores on the hip joint angle and the knee joint angle, estimator 33 estimates the ability level for the biomechanical constraints. For example, based on the score on the FRT, estimator 33 estimates the ability level for the stability limits and verticality. For example, based on the score on the time of standing on one leg with eyes open, estimator 33 estimates the ability level for the postural change. For example, based on the score on the time of standing on one leg with eyes open, estimator 33 may estimate the ability level for the anticipatory postural adjustments. For example, based on the score on the ratio of the standing on one leg with eyes open to the standing on one leg with eyes closed, estimator 33 estimates the ability level for the sensory function. For example, based on at least one of the scores on TUG and MCI, estimator 33 estimates the ability level for the stability in gait. The ability level may be represented by a numerical value or a level on a scale of levels.

Although estimator 33 estimates the ability level by reference to a table that associates a score with an ability level, the method of estimating the ability level is not limited to this.

Estimator 33 outputs the estimated physical ability level of user U to suggester 34.

Next, suggester 34 determines an intervention method for user U, based on the physical ability level of user U (S22). Next, outputter 35 outputs the estimated physical ability level and the determined intervention method to terminal device 50, and terminal device 50 obtains this ability level and the intervention method (S23). Note that at least the intervention method may be outputted in Step S23.

Next, terminal device 50 displays the physical ability level and the intervention method on display 51 (S24). This enables physical-ability estimation system 1 to notify user U via terminal device 50 about the intervention method appropriate to the gait feature of user U.

Note that the above-described estimation of the physical ability level may be made periodically. The at least two assessment items may be always the same on a per user-U basis. This allows changes (transitions) of the physical ability of user U to be found out. For example, an intervention method may be suggested according to an assessment item in which a noticeable change can be produced. The at least two assessment items may be designated each time, based on the biological information (for instance, the age) of user U, for example. With this, a situation of concern for the health of user U determined based on the biological information of user U can be found out by checking the score in the assessment item.

[3. Verification of Correlation]

The following describes verification performed on the estimation of the assessment items that can be made based on the gait feature estimated from the moving image, with reference to FIG. 6 to FIG. 14.

The estimation of the hip joint angle and the knee joint angle, which is an example of the assessment item, is described with reference to FIG. 6 to FIG. 8. FIG. 6 is a diagram illustrating a correlation between motion capture and moving image in hip joint angle estimation, according to the present embodiment. Note that each of FIG. 6 and FIG. 7 illustrates a correlation between the value in the assessment item based on the gait feature of user U obtained by motion capture and the value in the assessment item based on the gait feature of user U obtained using the three-dimensional frame model from the moving image.

In FIG. 6, the hip joint angle of user U based on the gait feature obtained by motion capture and the hip joint angle of user U based on the gait feature obtained based on the three-dimensional frame model from the moving image are represented by one point. FIG. 6 illustrates the plotted points corresponding to 108 persons, and also indicates correlation coefficients ("R" in this diagram).

More specifically, FIG. 6 is a diagram that plots: the hip joint angle obtained as a result of inputting the gait feature of user U obtained by motion capture into a learned model, which is trained to output a hip joint angle for an input of gait feature; and the hip joint angle obtained as a result of inputting the gait feature of user U obtained based on the moving image into the learned model. Correlation coefficient R is 0.713 and thus a correlation is present.

Here, assume that the hip joint angle obtained as a result of the inputting of the gait feature of user U obtained by motion capture is correct. In this case, the correct hip joint angle can be calculated based on the hip joint angle obtained as a result of the inputting of the gait feature of user U obtained based on the moving image. To be more specific, the hip joint angle of user U can be estimated from the moving image that captures user U walking.

FIG. 7 is a diagram illustrating a correlation between motion capture and moving image in knee joint angle estimation, according to the present embodiment.

In FIG. 7, the knee joint angle of user U based on the gait feature obtained by motion capture and the knee joint angle of user U based on the gait feature obtained based on the three-dimensional frame model from the moving image are represented by one point. FIG. 7 illustrates the plotted points corresponding to 108 persons, and also indicates correlation coefficients ("R" in this diagram).

More specifically, FIG. 7 is a diagram that plots: the knee joint angle obtained as a result of inputting the gait feature of user U obtained by motion capture into a learned model, which is trained to output a knee joint angle for an input of gait feature; and the knee joint angle obtained as a result of inputting the gait feature of user U obtained based on the moving image into the learned model. Correlation coefficient R is 0.577 and thus a correlation is present.

Here, assume that the knee joint angle obtained as a result of the inputting of the gait feature of user U obtained by motion capture is correct. In this case, the correct knee joint angle can be calculated based on the knee joint angle obtained as a result of the inputting of the gait feature of user U obtained based on the moving image. To be more specific, the knee joint angle of user U can be estimated from the moving image that captures user U walking.

FIG. 8 is a diagram illustrating an accuracy rate of estimation of normal range of gait motion based on a moving image, according to the present embodiment. FIG. 8 shows the accuracy rates of the estimated values of the hip joint angle and the knee joint angle obtained as a result of the inputting of the gait feature of user U obtained based on the moving image, assuming that the hip joint angle and the knee joint angle obtained as a result of the inputting of the gait feature of user U obtained by motion capture are correct. Here, $1\sigma$ (where $\sigma$ is a standard deviation) indicates the accuracy rate for the case where the estimated value is correct if a difference between the correct value and the estimated value is $1\sigma$ or smaller. Furthermore, $2\sigma$ indicates the accuracy rate for the case where the estimated value is correct if a difference between the correct value and the estimated value is $2\sigma$ or smaller.

As illustrated in FIG. 8, values close to the respective correct values of the hip joint angle and the knee joint angle are estimated at the rates of about 80% using 10 and at the rates above 90% using 20.

As described above, the correlation is present between: the hip joint angle and the knee joint angle estimated based on the moving image; and the hip joint angle and the knee joint angle estimated by motion capture. Thus, the hip joint angle and the knee joint angle can be estimated based on the gait feature estimated from the moving image.

The following describes the FRT and the rest, with reference to FIG. 9 to FIG. 14. Here, each of FIG. 9 to FIG. 14 illustrates verification of: the correlation between the value in the assessment item based on the gait feature of user U obtained by motion capture and the actual measured value in the assessment item; and the correlation between the value in the assessment item based on the three-dimensional frame model from the moving image and the actual measured value in the assessment item. Note that the same value is used as the actual measured values in the assessment item. Although "SVR Linear", "SVR RBF", "XGboost", and "Random Forest" are used in the verification as the algorithms for the learned models for estimating the assessment items in FIG. 9 to FIG. 14, the algorithms used are not limited to these. Any existing algorithms may be used as the algorithms for the learned models. In FIG. 9 to FIG. 14, "R" indicates a correlation coefficient and "MSE" indicates a mean square error.

Next, estimation of the FRT, which is an example of the assessment item, is described with reference to FIG. 9. FIG. 9 is a diagram illustrating a correlation between motion capture and moving image in the FRT estimation, according to the present embodiment. In FIG. 9, calculation is performed using data from 106 persons who performed the FRT.

Note that the results by motion capture and by the moving image are obtained as a result of inputting, into the learned model, the input information including: the gender, height, weight, age, gait cycle, gait speed, stride length, step length, and step width; the respective values obtained by dividing the stride length, the step length, and the step width by the height; and the value obtained by dividing the stride length by the step length.

As illustrated in FIG. 9, a correlation based on motion capture is present when the algorithms "SVR Linear", "XGboost", and "Random Forest" are used. The highest correlation coefficient is calculated using "SVR Linear". A correlation based on the moving image is present when the algorithms "SVR Linear" and "XGboost" are used. The highest correlation coefficient is calculated using "SVR Linear".

On account of this, "SVR Linear" may be used as the algorithm for the learned model (the third learned model, for example) in the FRT estimation. Note that similar MSE values are calculated based on both motion capture and the moving image.

Next, estimation of the time of standing on one leg with eyes open, which is an example of the assessment item, is described with reference to FIG. 10. FIG. 10 is a diagram illustrating a correlation between motion capture and moving image in the estimation of the time of standing on one leg with eyes open, according to the present embodiment. In FIG. 10, calculation is performed using data from 108 persons who performed the standing on one leg with eyes open. FIG. 10 illustrates the result of the estimation of the time of standing on one leg with eyes open that is logarithmically transformed by log 2 by adding the variability component (that is, the variability feature) of the gait.

Note that the results by motion capture and by the moving image are obtained as a result of inputting, into the learned model, the input information including: the gender, height, weight, age, gait cycle, gait speed, stride length, step length, and step width; the respective values obtained by dividing the stride length, the step length, and the step width by the height; and the value obtained by dividing the stride length by the step length. In addition to these, this input information also includes the variability feature of: the gait cycle, gait speed, stride length, step length, and step width; the respective values obtained by dividing the stride length, the step length, and the step width by the height; and the value obtained by dividing the stride length by the step length. Note that the variability feature is inputted to improve the correlation coefficients.

As illustrated in FIG. 10, the highest correlation coefficient based on motion capture is calculated using the algorithm "SVR Linear". The highest correlation coefficient based on the moving image is calculated using the algorithm "XGboost".

Although the correlation coefficients calculated for the time of standing on one leg with eyes open are below 0.5, similar correlation coefficients are calculated based on motion capture and the moving image. Thus, the estimation from the moving image can be performed with accuracy nearly equal to the accuracy achieved by motion capture.

On account of this, when the gait feature based on motion capture is inputted for the estimation of the time of standing on one leg with eyes open, "SVR Linear" may be used as the algorithm for the learned model (the fourth learned model, for example). Furthermore, when the gait feature based on the moving image is inputted for this estimation, "XGboost" may be used. Note that similar MSE values are calculated based on both motion capture and the moving image.

Next, estimation of the ratio of the standing on one leg with eyes open to the standing on one leg with eyes closed, which is an example of the assessment item, is described with reference to FIG. 11. FIG. 11 is a diagram illustrating a correlation between motion capture and moving image in the estimation of the ratio of the standing on one leg with eyes open to the standing on one leg with eyes closed, according to the present embodiment. In FIG. 11, calculation is performed using data from 108 persons who performed the standing on one leg with eyes open and the standing on one leg with eyes closed. FIG. 11 illustrates the result of the estimation of the time of standing on one leg that is logarithmically transformed by log 2 (with eyes open/with eyes closed) by adding the variability component (that is, the variability feature) of the gait.

Note that the results by motion capture and by the moving image are obtained as a result of inputting, into the learned model, the input information including: the gender, height, weight, age, gait cycle, gait speed, stride length, step length, and step width; the respective values obtained by dividing the stride length, the step length, and the step width by the height; and the value obtained by dividing the stride length by the step length. In addition to these, this input information also includes the variability feature of: the gait cycle, gait speed, stride length, step length, and step width; the respective values obtained by dividing the stride length, the step length, and the step width by the height; and the value obtained by dividing the stride length by the step length. Note that the variability feature is inputted to improve the correlation coefficients.

As illustrated in FIG. 11, the respective highest correlation coefficients based on motion capture and the moving image are calculated using the algorithm "Random Forest". Note that although the correlation coefficients for the ratio of the standing on one leg with eyes open to the standing on one leg with eyes close are below 0.5, the similar correlation coefficients are calculated based on motion capture and the moving image. Thus, the estimation from the moving image can be performed with accuracy nearly equal to the accuracy achieved by motion capture.

On account of this, "Random Forest" may be used as the algorithm for the learned model (the fifth learned model, for example) in the estimation of the ratio of the standing on one leg with eyes open to the standing on one leg with eyes close. Note that similar MSE values are calculated based on both motion capture and the moving image.

Next, estimation of the TUG, which is an example of the assessment item, is described with reference to FIG. 12. FIG. 12 is a diagram illustrating a correlation between motion capture and moving image in the TUG estimation, according to the present embodiment. In FIG. 12, calculation is performed using data from 108 persons who performed the TUG.

Note that the results by motion capture and by the moving image are obtained as a result of inputting, into the learned model, the input information including: the gender, height, weight, age, gait cycle, gait speed, stride length, step length, and step width; the respective values obtained by dividing the stride length, the step length, and the step width by the height; and the value obtained by dividing the stride length by the step length.

As illustrated in FIG. 12, a correlation based on motion capture is present when the algorithms "SVR Linear" and "Random Forest" are used. A correlation based on the moving image is present when the algorithms "XGboost" and "Random Forest" are used.

The correlation based on each of motion capture and the moving image is present when the algorithm "Random Forest" is used. Thus, the same algorithm can be used for both motion capture and the moving image.

On account of this, "Random Forest" may be used as the algorithm for the learned model (the sixth learned model, for example) in the TUG estimation. Note that similar MSE values are calculated based on both motion capture and the moving image.

Next, estimation about whether the user is healthy or suffering from MCI, which is an example of the assessment item, is described with reference to FIG. 13. FIG. 13 is a diagram illustrating an assessment result (area under the curve (AUC)) of the estimation about whether the user is healthy or suffering from MCI based on motion capture and the moving image (the number of gait features is 10), according to the present embodiment. In FIG. 13, calculation is performed using data from 81 persons who performed the mini-mental state examination (MMSE) test. Here, AUC indicates an assessment indicator for two-class classification. If AUC is 0.65 or higher, the present estimation method is determined to be good.

Note that the results by motion capture and by the moving image are obtained as a result of inputting, into the learned model, the input information including: the gender, height, weight, age, gait cycle, gait speed, stride length, step length, and step width; the respective values obtained by dividing the stride length, the step length, and the step width by the height; and the value obtained by dividing the stride length by the step length. The learned model performs binary classification to determine whether the user is healthy or suffering from MCI. More specifically, the learned model presents an output indicating whether user U is healthy or suffering from MCI.

As illustrated in FIG. 13, the AUC based on motion capture is above 0.65 when the algorithm "Random Forest" is used. Based on the moving image, no algorithm achieves the AUC above 0.65.

On account of this, for the estimation about whether the user is healthy or suffering from MCI by inputting the 10 gait features, the input information may include the gait features estimated based on motion capture and "Random Forest" may be used as the algorithm for the learned model (the seventh learned model, for example).

Here, the inventors found that the gait speed of a person suffering from MCI tended to be slower than that of a healthy person. Then, the inventors further performed verification of estimation about whether the user is healthy or suffering from MCI based on only the gait speed as the gait characteristic. The verification result is described with reference to FIG. 14. FIG. 14 is a diagram illustrating an assessment result (AUC) of the estimation about whether the user is healthy or suffering from MCI based on motion capture and the moving image (gait characteristic: only the gait speed), according to the present embodiment.

As illustrated in FIG. 14, the AUC based on motion capture is above 0.65 when the algorithms "SVR RBF" and "XGboost" are used. Furthermore, the AUC based on the moving image is 0.65 when the algorithm "XGboost" is used. By reducing the gait feature inputted into the learned model to only the gait speed, each of the AUCs based on motion capture and the moving image is improved.

Furthermore, each of the AUCs based on motion capture and the moving image is 0.65 or higher when the algorithm "XGboost" is used. Thus, the same algorithm can be used for both motion capture and the moving image.

On account of this, for the estimation about whether the user is healthy or suffering from MCI, only the gait speed may be inputted as the gait characteristic into the learned model (the seventh learned model, for example). Furthermore, "XGboost" may be used as the algorithm for the learned model for the estimation about whether the user is healthy or suffering from MCI. Note that similar MSE values are calculated based on both motion capture and the moving image.

As described thus far, the results on the assessment items can be estimated from the gait feature.

Advantageous Effects Etc

As described above, physical-ability estimation system 1 according to an aspect of the present invention includes: analyzer 32 (an example of the first estimator) that estimates a gait feature of a user from a moving image generated by capturing the user walking; and estimator 33 (an example of the second estimator) that estimates, based on the gait feature, respective assessment results on at least two assessment items for assessing a physical ability of the user.

With this, the respective assessment results (for example, the scores) on the at least two assessment items can be obtained based on the gait feature. For example, if an abnormality is found in the physical ability, the verification of the respective assessment results on the at least two assessment items enables estimation about which one of the assessment items relates to the abnormality. Thus, physical-ability estimation system 1 is capable of estimating a factor responsible for a problem with the physical ability. Since the factor can be estimated, intervention more suitable to user U can be expected.

It is possible that analyzer 32 estimates a frame of the user from the user shown in the moving image and, based on the frame estimated, estimates the gait feature.

With this, the respective assessment results on the at least two assessment items can be obtained based on the moving image of user U walking. More specifically, the assessment results can be easily obtained without preparing special-purpose equipment.

It is also possible that the user wears a marker, the moving image shows the user walking with the marker on is captured, and analyzer 32 estimates the gait feature, based on the marker shown in the moving image.

With this, the factor responsible for the problem with the physical ability can be estimated even from the gait feature obtained based on motion capture.

It is also possible that the at least two assessment items include a first item related to balance, the gait feature includes at least one of a gait cycle, a gait speed, a stride length, a step length, or a step width, and estimator 33 estimates the first item, based on the at least one of the gait cycle, the gait speed, the stride length, the step length, or the step width.

With this, if a problem is found in the physical ability, whether the factor responsible for the problem is related to balance can be estimated. Since the item related to balance is included among the assessment items, balance-related intervention more suitable to user U can be expected.

It is also possible that the at least two assessment items include a second item related to flexibility, the gait feature includes at least one of a hip joint angle or a knee joint angle, and estimator 33 estimates the second item, based on the at least one of the hip joint angle or the knee joint angle.

With this, if a problem is found in the physical ability, whether the factor responsible for the problem is related to flexibility can be estimated. Since the item related to flexibility is included among the assessment items, flexibility-related intervention more suitable to user U can be expected.

It is also possible that the at least two assessment items include a third item related to muscle strength, the gait feature includes a gait speed, and estimator 33 estimates the third item, based on at least the gait speed.

With this, if a problem is found in the physical ability, whether the factor responsible for the problem is related to muscle strength can be estimated. Since the item related to muscle strength is included among the assessment items, muscle-strength-related intervention more suitable to user U can be expected.

It is also possible that estimator 33 estimates respective scores in the at least two assessment items, as the respective assessment results.

With this, the assessment results can be expressed numerically. Thus, the simple checking of the scores enables an easy determination of the factor.

It is also possible that estimator 33 estimates the respective assessment results on the at least two assessment items, based also on a biological feature of the user.

With this, the assessment results estimated based also on the biological feature of user U can be obtained. For example, enhancement of the accuracy of the assessment results can be expected.

It is also possible that estimator 33 estimates the respective assessment results on the at least two assessment items, based also on an environmental feature indicating a walk environment of the user.

With this, the assessment results estimated based also on the environmental feature of user U can be obtained. For example, enhancement of the accuracy of the assessment results can be expected.

It is also possible that the at least two assessment items include at least two of: an ankle range of motion, FRT, standing on one leg with eyes open, standing on one leg with eyes closed, or TUG.

With this, the results on the assessment items related to balance can be estimated. For a reduced balance ability, the factor responsible for this can be estimated in detail.

A physical-ability estimation method according to another aspect of the present invention includes: estimating a gait feature of a user from a moving image generated by capturing the user walking (S19); and estimating, based on the gait feature, respective assessment results on at least two assessment items for assessing a physical ability of the user (S20). A non-transitory computer-readable recording medium having recorded thereon a computer program according to another aspect of the present invention causes a computer to execute the above-described physical-ability estimation method.

This achieves the same advantageous effects physical-ability estimation system 1 described above.

Other Embodiments

Although the physical-ability estimation system and the like according to one or more aspects of the present invention have been described based on the embodiment, the present invention is not limited to the embodiment. Those skilled in the art will readily appreciate that embodiments arrived at by making various modifications to the above embodiment or embodiments arrived at by selectively combining elements disclosed in the above embodiment without materially departing from the scope of the present invention may be included within one or more aspects of the present invention.

The above embodiments describe an example in which the balance ability, which is an example of the physical ability, is estimated based on the gait characteristic. However, the physical ability is not limited to the balance ability. For example, the physical ability may include muscle strength and flexibility. The control device may estimate lower-limb muscle strength information of the user, based on the knee angle of the user taking a forward step while walking in the moving image. The control device may estimate the lower-limb muscle strength information of the user, based on a change in the gait speed of the user stopping while walking in the moving image. In this way, the physical ability other than the balance ability may also be estimated from the gait feature.

For example, the assessment items on the physical ability may include a flexibility-related assessment item (an example of a second item), and the gait feature may include at least one of the hip joint angle and the knee joint angle. Then, the estimator may estimate the flexibility-related assessment item, based on the at least one of the hip joint angle and the knee joint angle.

For example, the assessment items on the physical ability may include a muscle-strength-related assessment item (an example of a third item), and the gait feature may include at least the gait speed. Then, the estimator may estimate the muscle-strength-related assessment item, based on the at least the gait speed.

Furthermore, an order of performing the steps (processes) in each of the flowcharts explained in the above embodiment is an example for explaining the present invention in detail. The steps may be performed in different orders. The order of the steps may be changed, or may be performed in parallel. Furthermore, a step performed by a certain processing unit may be performed by another processing unit. A part of the above steps may be performed with the other steps simultaneously (in parallel), or may be skipped.

The dividing of the functional blocks in each of the block diagrams is one example. It is possible that a plurality of functional blocks are implemented into a single functional block, that a single functional block is divided into a plurality of functional blocks, and that a function executed by a functional block is partially executed by another functional block. Furthermore, similar functions of a plurality of functional blocks may be executed by a single hardware or software in parallel or by time division.

Although the physical-ability estimation system according the above embodiment is implemented to a plurality of devices, it may be implemented to a single device. When the physical-ability estimation system is implemented to a plurality of devices, it is not limited how to allocate the constituent elements included in the physical-ability estimation system to the plurality of devices.

Although the control device according the above embodiment is implemented to a single device, it may be implemented to a plurality of devices. When the control device is implemented to a plurality of devices, it is not limited how to allocate the constituent elements included in the control device to the plurality of devices. The communication method between the plurality of devices is not limited. It may be wireless communication, wired communication, or a combination of wireless communication and wired communication.

Each of the constituent elements in the above embodiment and the like may be configured in the form of an exclusive hardware product, or may be realized by executing a software program suitable for the constituent element. Each of the constituent elements may be realized by means of a program executing unit, such as a Central Processing Unit (CPU) or a processor, reading and executing the software program recorded on a recording medium such as a hard disk or semiconductor memory.

It should be noted that each of the constituent elements explained in the above embodiment may be implemented to software, or typically implemented to a Large Scale Integration (LSI) which is an integrated circuit. The constituent elements may be integrated separately, or a part or all of them may be integrated into a single chip. LSI is described here, but the integrated circuit may also be referred to as an integrated circuit (IC), a system LSI circuit, a super LSI circuit or an ultra LSI circuit depending on the degree of integration. Moreover, the circuit integration technique is not limited to LSI, and may be realized by a dedicated circuit or a general purpose processor. After manufacturing of the LSI circuit, a field programmable gate array (FPGA) or a reconfigurable processor which is reconfigurable in connection or settings of circuit cells inside the LSI circuit may be used. Further, when development of a semiconductor technology or another derived technology provides a circuit integration technology which replaces LSI, as a matter of course, functional blocks may be integrated by using this technology.

The system LSI is a super multi-function LSI that is a single chip into which a plurality of constituent elements are integrated. More specifically, the system LSI is a computer system including a microprocessor, a Read Only Memory (ROM), a Random Access Memory (RAM), and the like. The ROM stores a computer program. The microprocessor operates according to the computer program, thereby causing the constituent element to execute its function.

It should be noted that general or specific aspects of the present invention may be implemented to a system, a device, a method, an integrated circuit, a computer program, or a computer-readable recording medium, such as a Compact Disc-Read Only Memory (CD-ROM). The general or specific aspects of the present invention may be implemented to any combination of a system, a device, a method, an integrated circuit, a computer program, and a recording medium. For example, the present invention may be a program for causing a computer to execute the physical-ability estimation system according to the above embodiment, or a non-transitory computer-readable recording medium that stores such a program. For example, such a program may be recorded onto a recording medium and distributed. For example, it is possible that such a distributed program is installed in a device having another processor and executed by the other processor so as to allow the other processor to perform the above-described steps of the processing.

REFERENCE SIGNS LIST

1 physical-ability estimation system
32 analyzer (first estimator)
33 estimator (second estimator)
U user

The invention claimed is:

1. A physical-ability estimation system comprising:

a first estimator that estimates a gait feature of a user from a moving image generated by capturing the user walking; and a second estimator that estimates, based on the gait feature, respective assessment results on at least two assessment items for assessing a physical ability of the user, the at least two assessment items including at least one of: Functional Reach Test (FRT), standing on one leg with eyes open, or standing on one leg with eyes closed, wherein:

the second estimator estimates the respective assessment results on the at least two assessment items by inputting the gait feature estimated by the first estimator into at least two models, the at least two models each corresponding to a corresponding assessment item among the at least two assessment items, the at least two models each receiving the gait feature as input and outputting an assessment result on the corresponding assessment item, the at least two assessment items include a first item related to balance and a second item related to flexibility, the gait feature includes at least one of a gait cycle, a gait speed, a stride length, a step length, a step width, a hip joint angle, or a knee joint angle, the second estimator estimates the first item based on the at least one of the gait cycle, the gait speed, the stride length, the step length, or the step width, and the second estimator estimates the second item based on the at least one of the hip joint angle or the knee joint angle.

2. The physical-ability estimation system according to claim 1, wherein the first estimator estimates a frame of the user from the user shown in the moving image and, based on the frame estimated, estimates the gait feature.

3. The physical-ability estimation system according to claim 1, wherein the user wears a marker, the moving image shows the user walking with the marker on is captured, and the first estimator estimates the gait feature, based on the marker shown in the moving image.

4. The physical-ability estimation system according to claim 1, wherein the at least two assessment items include a third item related to muscle strength, the gait feature includes a gait speed, and the second estimator estimates the third item, based on at least the gait speed.

5. The physical-ability estimation system according to claim 1, wherein the second estimator estimates respective scores in the at least two assessment items, as the respective assessment results.

6. The physical-ability estimation system according to claim 1, wherein the second estimator estimates the respective assessment results on the at least two assessment items, based also on a biological feature of the user.

7. The physical-ability estimation system according to claim 1, wherein the second estimator estimates the respective assessment results on the at least two assessment items, based also on an environmental feature indicating a walk environment of the user.

8. The physical-ability estimation system claim 1, wherein the at least two assessment items include at least two of: an ankle range of motion, the FRT, the standing on one leg with eyes open, the standing on one leg with eyes closed, or Timed Up and Go (TUG).

9. The physical-ability estimation system according to claim 1, wherein when estimating an abnormality in the physical ability based on the gait feature, the second estimator estimates a factor responsible for the abnormality based on the respective assessment results on the at least two assessment items.

10. A physical-ability estimation method comprising:

estimating a gait feature of a user from a moving image generated by capturing the user walking; and estimating, based on the gait feature, respective assessment results on at least two assessment items for assessing a physical ability of the user, the at least two assessment items including at least one of: Functional Reach Test (FRT), standing on one leg with eyes open, or standing on one leg with eyes closed, wherein the at least two assessment items include a first item related to balance and a second item related to flexibility, wherein the gait feature includes at least one of a gait cycle, a gait speed, a stride length, a step length, a step width, a hip joint angle, or a knee joint angle, and wherein estimating the respective assessment results on the at least two assessment items further includes:

inputting the gait feature into at least two models, the at least two models each corresponding to a corresponding assessment item among the at least two assessment items, the at least two models each receiving the gait feature as input and outputting an assessment result on the corresponding assessment item, estimating the first item based on the at least one of the gait cycle, the gait speed, the stride length, the step length, or the step width, and estimating the second item based on the at least one of the hip joint angle or the knee joint angle.

11. A non-transitory computer-readable recording medium having recorded thereon a computer program for causing a computer to execute the physical-ability estimation method according to claim 10.

* * * * *